(12) United States Patent
Howe

(10) Patent No.: US 9,468,509 B2
(45) Date of Patent: Oct. 18, 2016

(54) DENTAL CROWNS AND BRIDGES AND METHOD OF MAKING SAME

(71) Applicant: CMP INDUSTRIES LLC, Albany, NY (US)

(72) Inventor: Devon O. Howe, Saratoga Springs, NY (US)

(73) Assignee: CMP Industries LLC, Albany, NY (US)

( * ) Notice: Subject to any disclaimer, the term of this patent is extended or adjusted under 35 U.S.C. 154(b) by 299 days.

(21) Appl. No.: 14/212,645

(22) Filed: Mar. 14, 2014

(65) Prior Publication Data

US 2014/0272800 A1 Sep. 18, 2014

Related U.S. Application Data

(60) Provisional application No. 61/792,254, filed on Mar. 15, 2013.

(51) Int. Cl.
*A61C 13/00* (2006.01)
*A61C 13/083* (2006.01)
*A61C 13/08* (2006.01)
*A61C 13/09* (2006.01)
*A61C 5/08* (2006.01)

(52) U.S. Cl.
CPC ............ *A61C 13/0004* (2013.01); *A61C 5/08* (2013.01); *A61C 13/0003* (2013.01); *A61C 13/0022* (2013.01); *A61C 13/081* (2013.01); *A61C 13/083* (2013.01); *A61C 13/09* (2013.01); *Y10T 29/49567* (2015.01)

(58) Field of Classification Search
CPC .. A61C 5/10; A61C 13/0022; A61C 13/083; A61C 13/09; A61C 13/081; A61C 13/34; A61C 13/0003; A61C 13/0004; A61C 13/0006; B22F 3/12; B22F 3/162; B22F 2003/247; B22F 5/00; B22F 7/00; B22F 7/008; B22F 7/04; B22F 2007/042; B32B 2535/00; Y10T 29/49567; Y10T 29/49568; Y10T 29/49986; Y10T 29/49996
See application file for complete search history.

(56) References Cited

U.S. PATENT DOCUMENTS

| | | | |
|---|---|---|---|
| 2,514,076 A | 7/1950 | Kelly | |
| 3,126,429 A | 3/1964 | Saffir | |
| 4,392,829 A * | 7/1983 | Tanaka | A61C 5/08 433/208 |
| 4,937,928 A * | 7/1990 | van der Zel | A61C 9/00 29/896.1 |
| 4,970,032 A | 11/1990 | Rotsaert | |
| 5,151,044 A | 9/1992 | Rotsaert | |
| 5,672,305 A | 9/1997 | Kogure | |

(Continued)

*Primary Examiner* — Christopher Besler
*Assistant Examiner* — Matthew P Travers
(74) *Attorney, Agent, or Firm* — John M. Hammond; Patent Innovations LLC

(57) ABSTRACT

Dental prostheses and methods for making them are disclosed. In one embodiment, a method comprises a sequence of steps including milling a cavity in a block of a coping material, filling the cavity with a green ceramic material, milling a portion of the green ceramic material away to leave a layer of green ceramic material on an occlusal surface formed in the coping material, milling the underside of the block of coping material to form the coping with green ceramic material, and sintering the coping with green ceramic material to complete the prosthesis. The milling steps may be performed by a computer-controlled mill. The computer may execute a CAD-CAM program that includes data from a three dimensional model of a tooth that is to receive the prosthesis. The dental prosthesis may be a dental crown or a dental bridge.

15 Claims, 7 Drawing Sheets

(56) References Cited

U.S. PATENT DOCUMENTS

| | | |
|---|---|---|
| 6,488,503 B1 | 12/2002 | Lichkus et al. |
| 7,686,989 B2 | 3/2010 | Van der Zel |
| 7,981,531 B2 | 7/2011 | Rheinberger et al. |
| 8,641,938 B2 | 2/2014 | Howe |
| 2009/0026643 A1 | 1/2009 | Wiest et al. |
| 2012/0285019 A1* | 11/2012 | Schechner ......... A61C 13/0004 29/896.1 |

* cited by examiner

DENTAL CROWNS AND BRIDGES AND METHOD OF MAKING SAME

CROSS-REFERENCE TO RELATED PATENT APPLICATIONS

This application claims priority from U.S. provisional patent Application No. 61/792,254 filed Mar. 15, 2013, the disclosure of which is incorporated herein by reference.

BACKGROUND

1. Technical Field

Dental prostheses and apparatus and methods of manufacturing them. In particular, a dental crowns and bridges, and an associated CAD-CAM method for making the crowns and bridges.

2. Description of Related Art

Dentures, partial dentures, dental crowns, and dental bridges are prosthetic articles that are made to replace some or all of a person's natural teeth. A dental crown is a rigid fitting that completely encloses or caps a tooth or multiple teeth. A dental bridge is an artificial tooth or teeth that replaces missing natural teeth and that is joined to adjacent remaining teeth.

When a dentist diagnoses that his/her patient has a need for a dental crown or bridge, he/she will generally prepare the tooth (or teeth in the case of a bridge) to receive the crown or bridge by grinding the tooth with a suitable tool such as a high speed rotating diamond bur (also spelled "burr" in some sources). The bur is used to remove tooth structure that is decayed or to provide space that will be occupied by the crown or bridge. The dentist then obtains an accurate impression of the patient's existing gums and prepared teeth, including the tooth or teeth that will receive the crown or bridge, by using a silicone elastomer such as polyvinyl siloxane. The impression is then sent to a dental laboratory that specializes in manufacturing custom dental prosthetics for their customers who are dentists or other dental laboratories.

The field of fixed dental prosthetics, such as crowns and bridges, has evolved rapidly. In the 1960's, the standard of care was a porcelain-fused-to-metal (PFM) type crown. The porcelain used was typically feldspathic, i.e., made from feldspar mineral, and the metals used were gold-based alloys. A problem with the conventional feldspathic PFM is that the porcelain is very durable and tends to wear opposing natural dentition. In addition, metal can show through around the marginal edges of the porcelain, resulting in there being the perceived appearance of "black" lines at the margins.

In the 1980's, newer classes of porcelains were developed that were "low-fusing," which were "softer" than conventional feldspathic porcelains. The advantage of these porcelains was that the material was less abrasive to opposing natural dentition.

In the 1990's, all-ceramic fixed restorations were introduced. The advantage of this class of restorations was improved aesthetics, since no metal was used underneath the porcelain. The problem with many of these all-ceramic products was that they lacked strength, especially needed in the posterior teeth. Crowns made by computer aided design (CAD) and computer aided manufacturing (CAM) were also introduced. This approach reduced the expertise and labor costs required for conventional crowns.

In the late 1990's, fixed restorations were also made with an alumina substructure and overlaid with porcelain. This approach solved the problem with potential exposure of metal at the margins while also providing the crown or bridge with the required strength.

In the 2000's, zirconia was introduced as a substructure because it provided increased strength that was sufficient for posterior applications. Porcelain was still used to overlay the zirconia because the base color of zirconia at that time was white. The cost of milling zirconia by CAD-CAM based tooling was relatively expensive at the initial stage. However, the cost of milling equipment and software continued to decrease, such that more dental laboratories started using zirconia as the primary substructure for crowns. The primary problem with zirconia is the inherent color: it is bright white and does not have the appearance of natural teeth. Since most teeth are not completely white, some skill and cost is required to overlay porcelain on the zirconia in order to deliver an esthetic natural appearing tooth.

In the 2010's, zirconia has evolved and is now available in more translucent colors, in addition to more natural-looking tooth shades. Most recently, zirconia is being used for "full-contour" crowns, especially in the posterior region. "Full-contour" means that a porcelain overlay is not required on top of the zirconia. This evolution means that very little direct labor is required to make the crown. The only labor required is the person(s) executing the software program, supervising the automated milling operation, and finishing/inspecting the resulting crown product.

Many dental laboratories have embraced this approach because of the low production costs. However, certain problems remain to be solved with this manufacturing method and/or with the dental prostheses made by it. One remaining problem is that the zirconia is very abrasive to the opposing dentition, which was the original problem with conventional feldspathic PFMs. One countermeasure is to use the shaded or translucent zirconia as the base material, and then place "low-fusing" porcelain on top of the zirconia. The procedure is performed by dental labs today, especially in the anterior (front) teeth to give the appearance of multi-layers which enhance esthetics. However, a problem with this approach is that it requires skills and labor to layer the porcelain by hand, which makes the crown more expensive to produce.

Thus there remains a need for a method of making a dental crown or bridge that is of low cost, that uses materials resistant to wear and having a desired aesthetic appearance, and that is amenable to automation via the use of CAD-CAM software and CAD-CAM operated machines.

SUMMARY

In one aspect of the invention, there is provided a method to create a dental crown and dental bridge using a CAD-CAM milling technique. In the method, a disc of shaded zirconia is placed in a milling machine and is cut only on the occlusal side of the disc to reflect the contour of a prepared tooth. Then the void created is filled with "low-fusing" synthetic porcelain. Next, the porcelain is densified by pressing it into the zirconia with pneumatic or mechanical means. Lastly, the milling machine is instructed by the CAM software to remove the excess porcelain and underside of the zirconia to reveal the semi-finished crown.

In another aspect of the invention, there is provided a method of making a dental prosthesis. The method comprises forming a first cavity in a first surface of a block of solid material, the first cavity having a bottom surface comprising a protrusion extending upwardly and shaped to correspond to an occlusal surface of the dental prosthesis;

filling the first cavity with a green ceramic material; applying pressure to the green ceramic material, thereby densifying the green ceramic material; removing a first portion of the green ceramic material from the first cavity such that the remaining portion forms a layer of green ceramic material contiguous with the protrusion of the bottom surface of the first cavity and having a contour that corresponds to the shape of the protrusion; forming a second cavity in a second surface of the block of solid material, the second surface opposed to the first surface, the second cavity having an inner surface shaped to correspond to the surface of a tooth that is to receive the dental prosthesis and that corresponds to the protrusion of the bottom surface of the first cavity, thereby forming a coping made of the solid material and contiguous with the layer of green ceramic material and including the inner surface shaped to correspond to the surface of a tooth that is to receive the dental prosthesis; and sintering the coping and layer of green ceramic material to form the dental prosthesis.

The method may further comprise producing a three dimensional virtual model of the tooth that is to receive the dental prosthesis, and using data from the virtual model to define the shape of the inner surface of the coping. Producing the three dimensional virtual model is comprised of making a solid replica of the tooth that is to receive the dental prosthesis, scanning the solid replica to obtain three dimensional data of the replica, and defining the three dimensional virtual model from the three dimensional data of the replica.

Forming the first cavity in the first surface of the block of solid material, removing the first portion of the green ceramic material from the first cavity, and forming the second cavity in the second surface of the block of solid material may be performed by a mill. The mill may be controlled by a computer. The computer of the mill may uses data from a three dimensional virtual model of a solid replica of the tooth that is to receive the dental prosthesis in executing a program to control the forming the first cavity in the first surface of the block of solid material, removing the first portion of the green ceramic material from the first cavity, and forming the second cavity the second surface of the block of solid material.

The solid material may be a composite material, or a ceramic material such as zirconia. The green ceramic material may be porcelain, such as low fusing synthetic porcelain.

In another aspect of the invention, there is provided dental prostheses made by the methods disclosed herein. The dental prostheses include dental bridges and dental crowns.

Advantageously, the methods described herein solve several problems associated with current methods of making a crown or bridge dental prosthesis, including reducing inconsistencies of human "artistry" that are applied to the hand-layered porcelain that forms the visible outer layer of the crown or bridge. Labor costs for the manufacturing of the prosthesis are also reduced.

BRIEF DESCRIPTION OF THE DRAWINGS

The present disclosure will be provided with reference to the following drawings, in which like numerals refer to like elements, and in which.

Figure 1A:
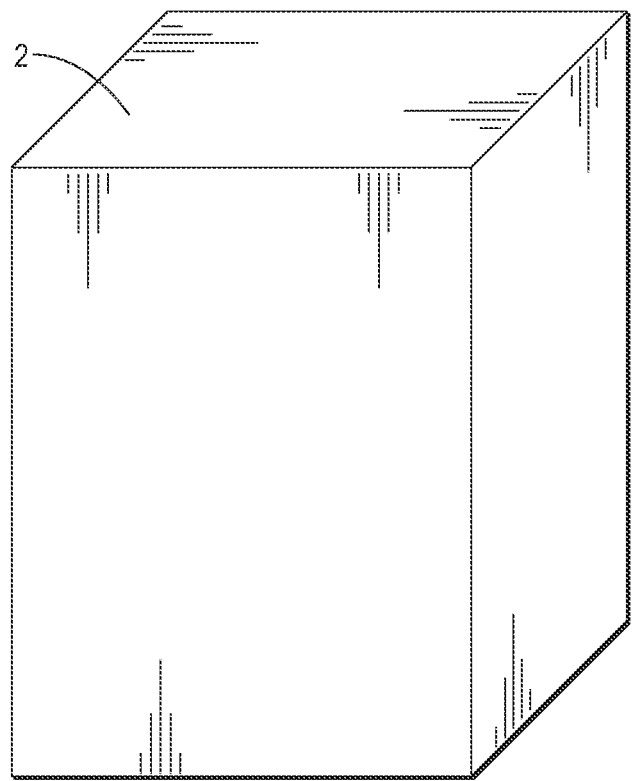
FIG. 1A is a perspective view of a three-dimensional volume that may contain a physical model of a patient's tooth to be scanned by a 3D scanner.

The present invention will be described in connection with certain preferred embodiments. However, it is to be understood that there is no intent to limit the invention to the embodiments described. On the contrary, the intent is to cover all alternatives, modifications, and equivalents as may be included within the spirit and scope of the invention as defined by the appended claims.

DETAILED DESCRIPTION

For a general understanding of the present invention, reference is made to the drawings. In the drawings, like reference numerals have been used throughout to designate identical elements. In the following disclosure, certain components may be identified with adjectives "top," "upper," "bottom," "lower," "left," "right," etc. These adjectives are provided in the context of the orientation of the drawings, which is arbitrary. The description is not to be construed as limiting the methods and apparatus disclosed herein to use in a particular spatial orientation. The instant methods and apparatus may be used in orientations other than those shown and described herein.

As used herein, the term or acronym "CAD-CAM" refers to Computer Aided Design and Computer Aided Manufacturing. Depending upon the context of use, the term may be referring to a computer software program for the design of an article such as a tooth or denture, or a computer software program for the manufacture of an article such as a tooth or denture; or a combination of both. The term may also be used with reference to a machine, which is used to manufacture an article such as a tooth or denture, and which is controlled by a computer that executes such computer software program(s).

Turning first to FIG. 1A, a three-dimensional volume that may contain a physical model, i.e., a replica of a patient's tooth to be scanned by a 3D scanner is depicted. The patient's tooth is typically degraded for some reason, and requires medical intervention by a dentist in order to preserve the tooth, rather than simply extracting it. The dentist may prepare the tooth by removing degraded material with dental tools, leaving behind material that is in good enough condition to receive a crown or bridge.

To make a physical model of the tooth, an impression of the tooth is obtained in a pliable material. The impression is used as a mold for receiving dental stone, which then hardens into a solid replica of the patient's tooth to receive the crown or bridge.

Figure 1B:
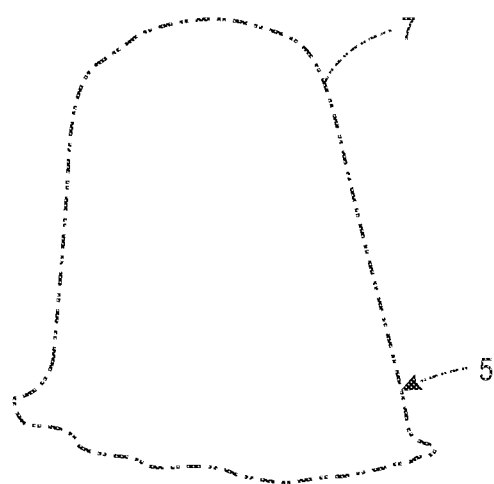
FIG. 1B is a two-dimensional rendering of a virtual model created from scanning the physical model of the patient's tooth.

The patient's tooth, which occupies the volume 2 depicted in FIG. 1A, is scanned in the three dimensions defined by the edges of the volume 2 by a 3D scanner (not shown), such as a 4 or 5-axis scanner that is used to obtain three-dimensional data from a solid object and create a virtual model of the object. The three dimensional data from the scanner is acquired and processed by a computer (not shown) that executes Computer Aided Design software to produce a virtual model 5 of the tooth as depicted in FIG. 1B. The virtual model 5 is then used to make a dental prosthesis for fitting to the tooth as will now be described.

In a first step, the three dimensional data from the scanner is used to design the contour, thickness and margins of a coping that will fit over the stone model. The three dimensional data may be used by CAD software to design the coping.

Figure 2:
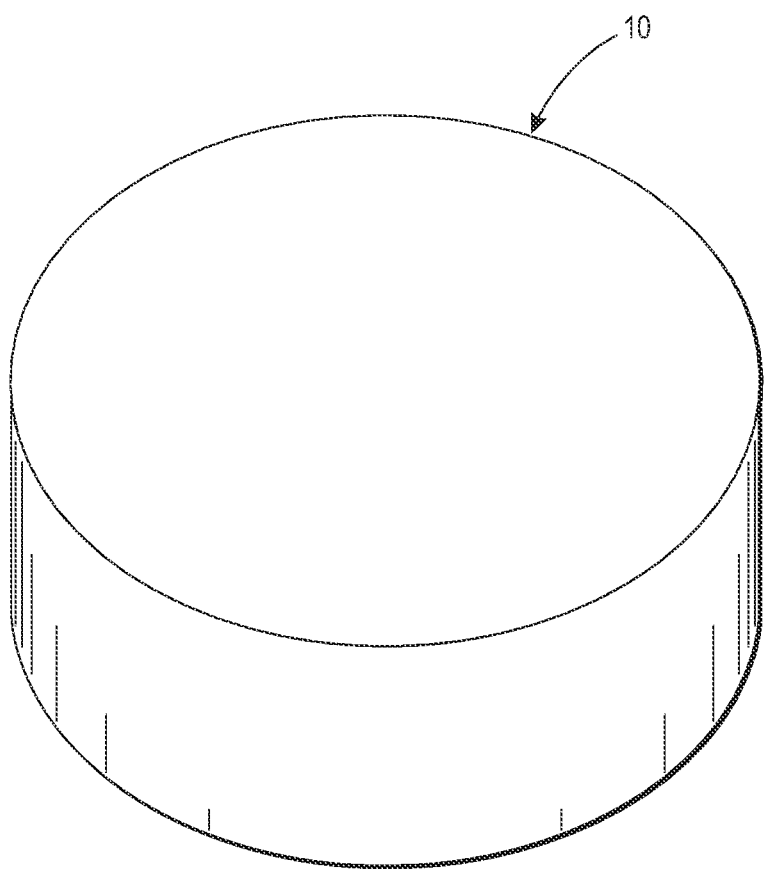
FIG. 2 is a upper perspective view of a disc of starting material, which may be zirconia, used in making dental prostheses.

Referring now to FIG. 2, a block or disc of starting material used in making a dental prosthesis is depicted. The block or disc may be of zirconia material, which may be a shaded zirconia, or a translucent zirconia. Although the disc may be referred to subsequently herein as a "zirconia disc," it is to be understood that the material for the disc is not limited exclusively to zirconia. The disc may be of another solid material, such as another ceramic material or a composite material. The disc undergoes a series of processing steps to make the dental prosthesis as shown in FIGS. 3-7. Although fabrication of a dental prosthesis for a single tooth is shown in FIGS. 3-7, with the dental prosthesis being a crown, it is to be understood that the methods of the present disclosure are applicable to making dental prostheses for multiple teeth, such as a bridge prosthesis.

Figure 3:
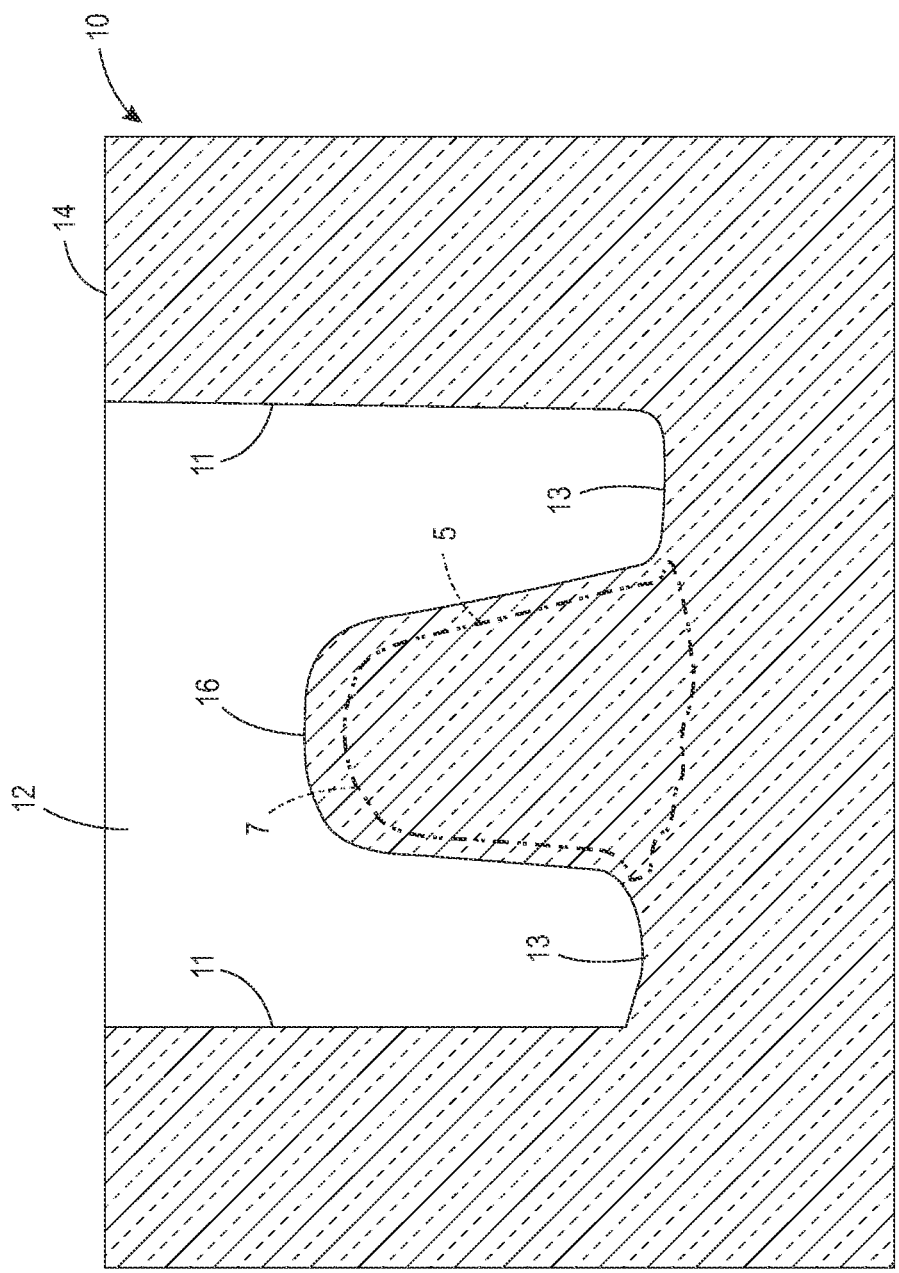
FIG. 3 is a cross-sectional view of the zirconia disc after a first milling operation.

Referring to FIG. 3, a first step of fabrication of the coping to be fit over the stone tooth model (and eventually the patient's tooth) is shown, in which the zirconia disc undergoes a first milling operation. A CAD-CAM milling machine (not shown) cuts a first cavity 12 in the top surface 14 of the zirconia disc 10. For the sake of simplicity of illustration, details of the CAD-CAM milling machine, such as a framework, turret, mill bed, motors, collet chuck, milling bit, and drives are not shown in FIGS. 3-7. Such details are known to those skilled in the art of Computer Numerical Control (CNC) milling machines. Additionally, relevant details of milling processes may be found in the Applicant's commonly owned U.S. Pat. No. 8,641,938, which discloses a method of making a denture. The method includes certain steps for milling denture base materials and artificial tooth materials. The disclosure of this United States patent is incorporated herein by reference.

The first void or cavity 12 is cut to form the occlusal side of the coping to be made. The cavity has a side wall 11 and a bottom surface 13. The bottom surface 13 of the cavity 12 has a protrusion 16 extending upwardly and forming the occlusal side (facing opposing teeth) of the eventual coping. The geometric profile of the protrusion 16 is such that it is slightly larger than the corresponding profile 7 of the virtual model 5 of the patient's tooth, which is to receive the finished prosthesis. Thus the protrusion 16 is also shaped to correspond to the occlusal surface of the eventual finished prosthesis, but will be separated from the occlusal surface by a layer of material that will form the coping, as will be explained subsequently. In other words, the protrusion 16 follows a rough outline of the occlusal surface, but is slightly smaller dimensionally. The three-dimensional data of the virtual model 5 (shown in dotted line in FIGS. 3-6) is used by the CAD-CAM milling program to control the cutting by the milling bit in a manner that results in the protrusion 16 being slightly larger than the upper edge profile of the virtual model 5.

Figure 4:
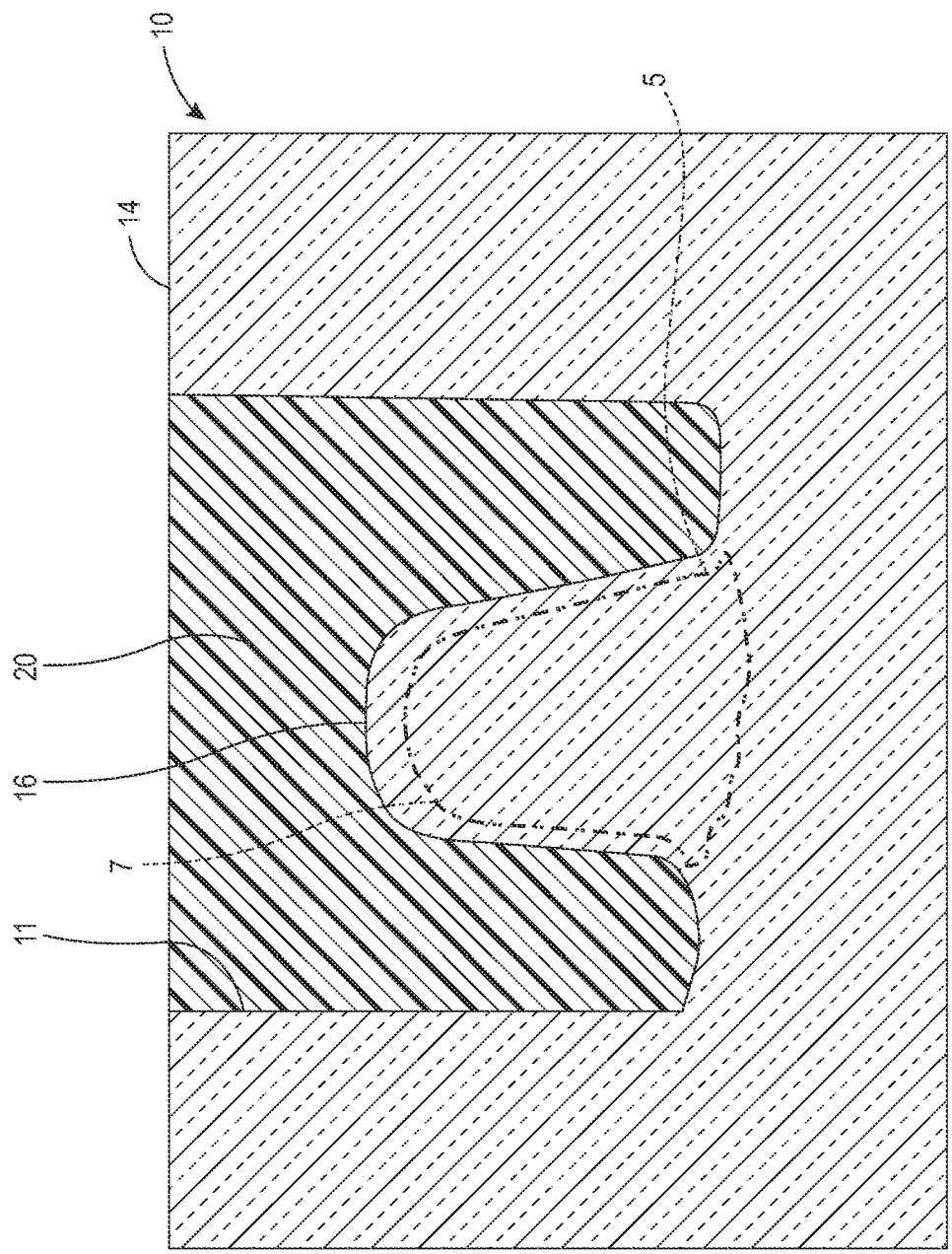
FIG. 4 is a cross-sectional view of the zirconia disc, with "green" ceramic material having been added to the cavity formed by the first milling operation.

Referring to FIG. 4, the cavity 12 is filled with an uncured "green" (i.e. not fired or sintered) ceramic material 20. The green ceramic material 20 may be "low-fusing" synthetic porcelain in a flowable form.

Figure 5:
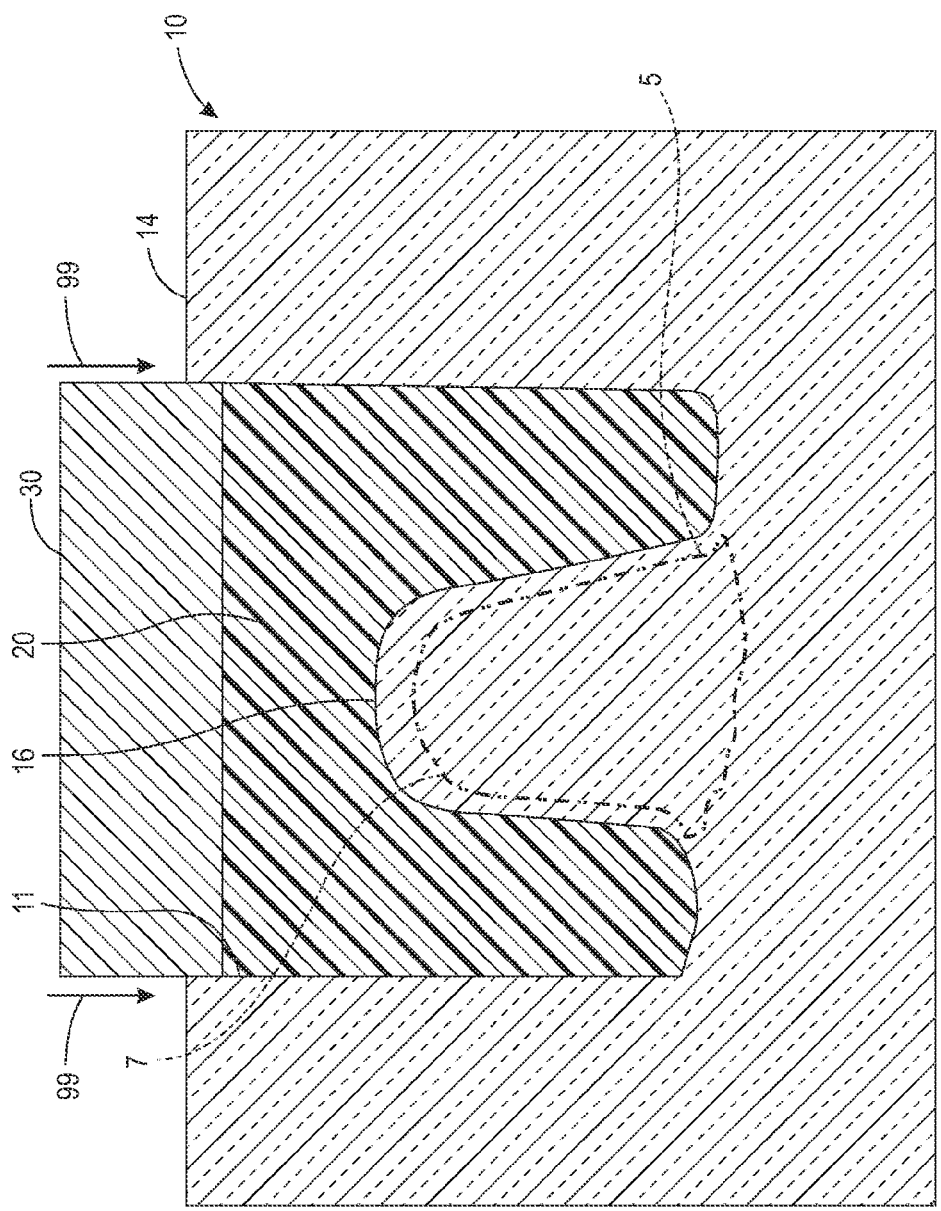
FIG. 5 is a cross-sectional view of an instrument applying pressure to the green ceramic material in the cavity.

Referring to FIG. 5, an instrument is used to apply pressure to the green ceramic material 20 contained in the cavity 12. The instrument may be a press (not shown) that forces a block 30 downwardly into the cavity 12 using suitable pneumatic or mechanical means as indicated by arrows 99. In the milling operation of FIG. 3, the side wall 11 of the cavity 12 is cut by the mill such that it has a perimeter that will receive the block 30 and allow the block 30 to be pushed down into the cavity 12, thereby applying pressure to the material 20. The applied pressure densifies (i.e., increases the density of) and hardens the low-fusing synthetic porcelain 20 or other green ceramic material 20 in the cavity 12.

Figure 6:
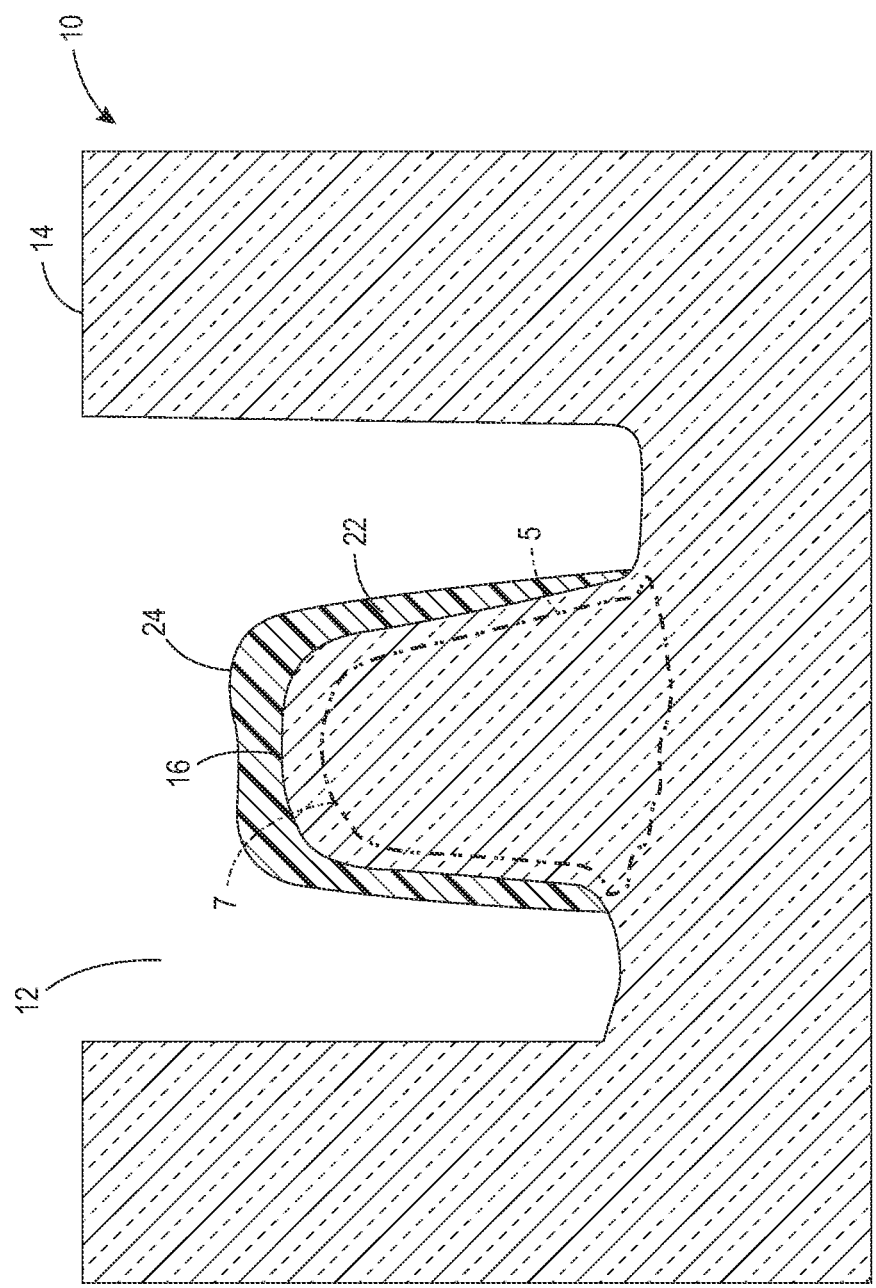
FIG. 6 is a cross-sectional view of the zirconia disc after removing un-needed green ceramic material from the cavity in a second milling operation.

Referring to FIG. 6, the block 30 has been removed from the cavity 12, and a second milling operation has been performed by the CAD-CAM mill in which un-needed green ceramic material has been removed from the cavity 12. The portion 22 of green ceramic material that is left behind has been cut back to provide a final contour 24 of the occlusal side of the eventual prosthesis to be produced. The contour 24 of the green ceramic material portion 22 corresponds to the contour of the protrusion 16 that was milled previously from the zirconia disc, which in turn corresponds to the profile 7 of the virtual model 5 of the patient's tooth as described previously.

Figure 7:
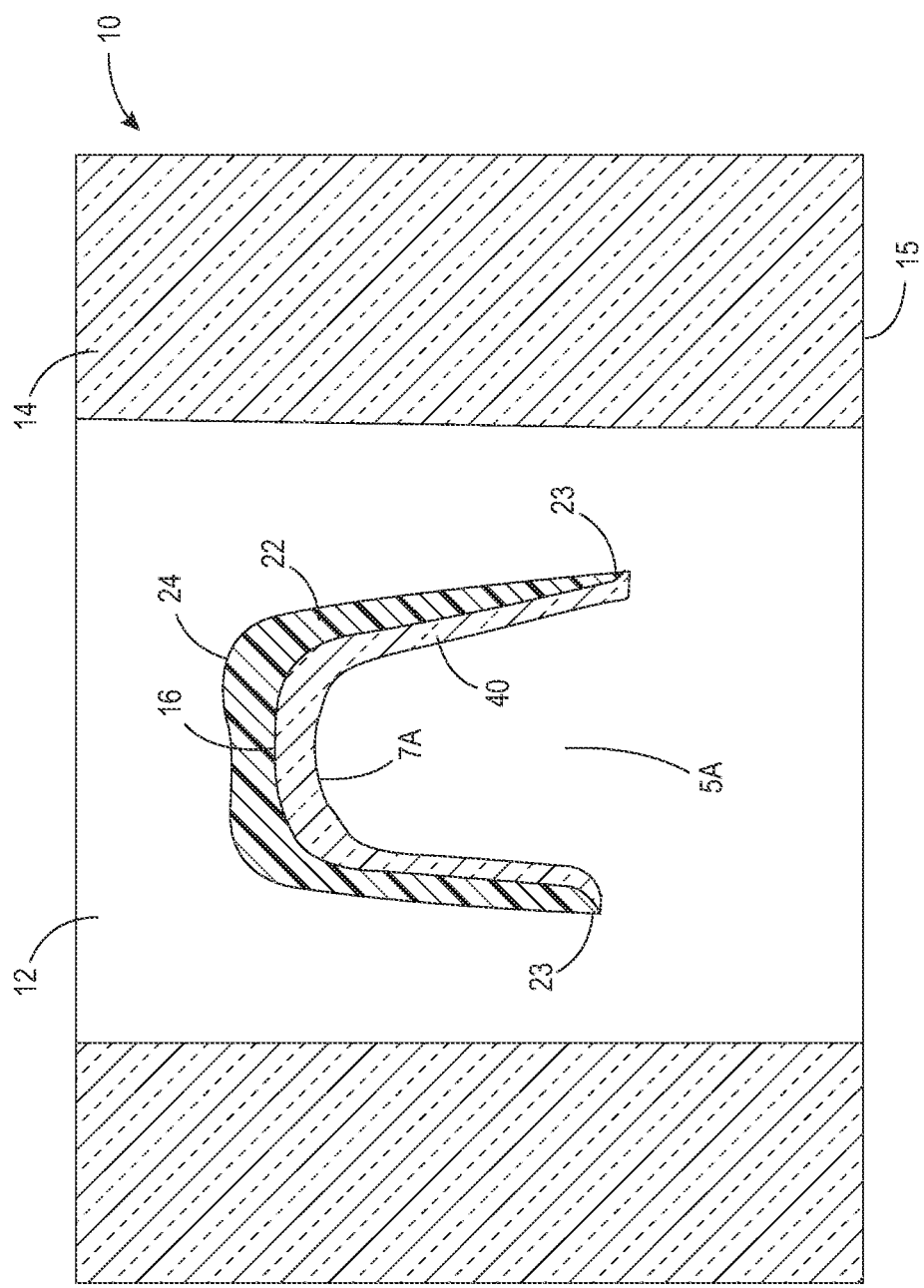
FIG. 7 is a cross-sectional view of the zirconia disc and a resulting partially finished prosthesis after milling the underside of the disc.

Referring to FIG. 7, a third milling operation has been performed in which the underside 15 of the zirconia disc has been cut away. All of the zirconia below the lowermost edge 23 of the portion 22 of remaining green ceramic material has been removed in the third milling operation. Additionally, a portion of zirconia that occupied a volume 5A that corresponds to the three dimensional data of the virtual model 5 of the tooth to receive the prosthesis has also been cut away. The zirconia that is left behind forms a coping 40 having a concave profile 7A that encloses the volume 5A, and that has the profile 7 of the virtual model 5 of the patient's tooth. In that manner, the coping 40 will have an effective fit with the patient's tooth when applied thereto.

It will be apparent that during the third milling operation, support structures may be left in the zirconia proximate to the lower most edge 23 of the portion 22 of remaining green ceramic material, so as to enable completion of the entire milling operation. The support structures may be the last portion of the zirconia to be removed, or may be made thin enough so that they can be fractured when removing the finished coping 40 and portion 22 of remaining green ceramic material.

In a subsequent operation (not shown), the milled piece comprising the finished coping 40 and portion 22 of green ceramic material are placed in a sintering furnace, and the portion 22 of green ceramic material is sintered to form the final ceramic material. In a subsequent operation (not shown), the sintered object may be polished using a high speed hand piece or other suitable tool to produce the final prosthesis. As described previously, this exemplary prosthesis is a crown, and may be comprised of a coping made of zirconia, and a ceramic outer layer made of porcelain.

In a further embodiment of the method of making a dental prosthesis, during the second milling operation, the porcelain or other green ceramic material may be cut away further than shown in FIG. 6, such that the thickness of the remaining portion 22 of green ceramic material is less than shown in FIG. 6. Then the cavity 12 may be filled with a second porcelain or other green ceramic material, compacted as shown in FIG. 5, and milled as shown in FIG. 6 to the final contour 16. In that manner, a two layer effect may be created that has the appearance closer to that of a natural tooth.

It is, therefore, apparent that there has been provided, in accordance with the present invention, a method for making dental crowns and bridges, and dental crowns and bridges made according to such methods. Having thus described the basic concept of the invention, it will be rather apparent to those skilled in the art that the foregoing detailed disclosure is intended to be presented by way of example only, and is not limiting. Various alterations, improvements, and modifications will occur to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims.

I claim:

1. A method of making a dental prosthesis, the method comprising
   a) forming a first cavity in a first surface of a block of solid material, the first cavity having a bottom surface comprising a protrusion extending upwardly and shaped to correspond to an occlusal surface of the dental prosthesis;
   b) filling the first cavity with a green ceramic material;
   c) removing a first portion of the green ceramic material from the first cavity such that a remaining portion forms a layer of green ceramic material contiguous with the protrusion of the bottom surface of the first cavity and having a contour that corresponds to the shape of the protrusion;
   d) forming a second cavity in a second surface of the block of solid material, the second surface opposed to the first surface, the second cavity having an inner surface shaped to correspond to the surface of a tooth that is to receive the dental prosthesis and that corresponds to the protrusion of the bottom surface of the first cavity, thereby forming a coping made of the solid material and contiguous with the layer of green ceramic material and including the inner surface shaped to correspond to the surface of a tooth that is to receive the dental prosthesis; and
   e) sintering the coping and layer of green ceramic material to form the dental prosthesis.

2. The method of claim 1, further comprising producing a three dimensional virtual model of the tooth that is to receive the dental prosthesis, and using data from the virtual model to define the shape of the inner surface of the coping.

3. The method of claim 2, wherein producing the three dimensional virtual model is comprised of making a solid replica of the tooth that is to receive the dental prosthesis, scanning the solid replica to obtain three dimensional data of the replica, and defining the three dimensional virtual model from the three dimensional data of the replica.

4. The method of claim 1, wherein the forming the first cavity in the first surface of the block of solid material, the removing the first portion of the green ceramic material from the first cavity, and the forming the second cavity in the second surface of the block of solid material are performed by a mill.

5. The method of claim 4, wherein the mill is controlled by a computer.

6. The method of claim 5, wherein the computer of the mill uses data from a three dimensional virtual model of a solid replica of the tooth that is to receive the dental prosthesis in executing a program to control the forming the first cavity in the first surface of the block of solid material, removing the first portion of the green ceramic material from the first cavity, and forming the second cavity the second surface of the block of solid material.

7. The method of claim 1, further comprising applying pressure to the green ceramic material, thereby densifying the green ceramic material prior to removing a first portion of the green ceramic material from the first cavity.

8. The method of claim 1, further comprising polishing the dental prosthesis following sintering.

9. The method of claim 1, wherein the solid material is a ceramic material.

10. The method of claim 9, wherein the ceramic material is zirconia.

11. The method of claim 1, wherein the green ceramic material is porcelain.

12. The method of claim 11, wherein the porcelain is a flowable low fusing synthetic porcelain.

13. The method of claim 1, wherein the solid material is zirconia, and the green ceramic material is synthetic porcelain.

14. The method of claim 1, wherein the dental prosthesis is a dental crown.

15. The method of claim 1, wherein the dental prosthesis is a dental bridge.

* * * * *